United States Patent
Chen et al.

(10) Patent No.: US 9,126,912 B1
(45) Date of Patent: Sep. 8, 2015

(54) PROCESSES FOR PREPARING FORMALDEHYDE, GLYCOLALDEHYDE AND ETHYLENE GLYCOL

(71) Applicants: Chien-An Chen, Hsin Chu (TW); Yi-Wen Chen, Hsin Chu (TW)

(72) Inventors: Chien-An Chen, Hsin Chu (TW); Yi-Wen Chen, Hsin Chu (TW)

(*) Notice: Subject to any disclaimer, the term of this patent is extended or adjusted under 35 U.S.C. 154(b) by 0 days.

(21) Appl. No.: 14/464,696

(22) Filed: Aug. 20, 2014

(30) Foreign Application Priority Data

Apr. 30, 2014 (TW) ............... 103115466 A

(51) Int. Cl.
| | | |
|---|---|---|
| C07C 45/64 | (2006.01) | |
| C07C 29/00 | (2006.01) | |
| C07C 47/19 | (2006.01) | |
| C07C 29/38 | (2006.01) | |
| C07C 47/04 | (2006.01) | |
| B01J 31/24 | (2006.01) | |

(52) U.S. Cl.
CPC ............. *C07C 47/19* (2013.01); *B01J 31/2409* (2013.01); *C07C 29/38* (2013.01); *C07C 47/04* (2013.01); *B01J 2231/44* (2013.01); *B01J 2531/821* (2013.01); *B01J 2531/822* (2013.01)

(58) Field of Classification Search
CPC ............................. C07C 45/64; C07C 29/141
USPC .......................... 568/458, 462, 862
See application file for complete search history.

(56) References Cited

U.S. PATENT DOCUMENTS

| | | | |
|---|---|---|---|
| 4,321,414 A * | 3/1982 | Costa ............................ | 568/862 |
| 4,362,820 A * | 12/1982 | Kaplan ......................... | 518/700 |
| 4,405,821 A * | 9/1983 | Goetz ............................ | 568/862 |
| 4,503,260 A * | 3/1985 | Auvil et al. .................. | 568/462 |
| 7,511,178 B2 * | 3/2009 | Almeida Lenero et al. .. | 568/852 |

* cited by examiner

*Primary Examiner* — Sikarl Witherspoon
(74) *Attorney, Agent, or Firm* — IPR Works, LLC

(57) ABSTRACT

A process for preparing ethylene glycol comprising: forming intermediums of formaldehyde and glycolaldehyde to synthetize ethylene glycol by reacting methanol with methanol in the presence of a catalyst composition comprising rhodium catalysts and ruthenium catalysts at a temperature between 50-150° C. and a pressure between 0-40 kg/cm²G.

7 Claims, No Drawings

PROCESSES FOR PREPARING FORMALDEHYDE, GLYCOLALDEHYDE AND ETHYLENE GLYCOL

BACKGROUND OF THE INVENTION

1. Field of the Invention

The invention relates to processes for preparing formaldehyde, glycolaldehyde and ethylene glycol, and more particularly to processes for preparing formaldehyde, glycolaldehyde and ethylene glycol by employing methanol.

2. Related Art

Ethylene glycol being a simple glycol is colorless, odorless and sweet liquid which can be mixed with water in any proportion. Ethylene glycol is used as solvents and raw materials for synthesizing polyester resins. Ethylene glycol is also used to manufacture antifreeze and thawing agents used in cars, planes and boats, or used to manufacture hydraulic brake, Inkpad and Ink used in pens and printing shops, etc.

In recent years, due to improved shale gas mining technology, a new process for preparing ethylene glycol by using ethylene in the shale gas is provided which comprises the followings steps: obtaining ethylene from shale gas; forming ethylene oxide ($C_2H_4O$) by reacting ethylene with oxygen in the presence of a silver (Ag) catalyst; forming ethylene glycol by reacting ethylene oxide with water in acid environment. Compared with the older process for preparing ethylene glycol, the cost of ethylene glycol prepared from the above-mentioned new process noticeably comes down and is about 0.7 USD/Kg. This causes a significant impact on those ethylene glycol producers located in the country or region that do not have the natural resources of shale gas.

Another process for preparing ethylene glycol is also provided which comprises the following steps. (a) Formaldehyde and water are formed by reacting methanol with oxygen at 300° C. in the presence of molybdenum (Mo) and iron (Fe) catalysts. (b) Anhydrous formaldehyde is obtained from the distillation of a mixture of the water and the formaldehyde at a pressure of about 4 kg/cm$^2$G at a temperature of about 150° C. (c) Glycolaldehyde is obtained by reacting the formaldehyde with carbon monoxide and hydrogen in about 2 hours in the presence of xylene and a rhodium (Rh) catalyst at a temperature of about 100° C. at a pressure of about 150 kg/cm$^2$G. In the step (c), the production and selectivity to glycolaldehyde is above 81% and 90%. For more information on the step (c), please refer to U.S. Pat. No. 7,511,178B2. (d) Ethylene glycol is obtained by reacting the glycolaldehyde with hydrogen in the presence of a nickel (Ni) catalyst at a temperature of about 40° C. at a pressure of about 50 kg/cm$^2$G. In the step (d), the production to ethylene glycol product is above 90%. The cost of ethylene glycol prepared from this process is about 0.7 USD/Kg, which is close to the cost of ethylene glycol prepared from shale gas. However, this process needs more steps, and has to apply the reaction gases of different step in different reaction chambers. Since the production steps of this process are more complicated, this process cannot surpass the process of preparing ethylene glycol by using shale gas.

In view of this, an improved process for preparing ethylene glycol is needed which has simplified production steps and a reduced cost of preparing ethylene glycol, so that it can surpass the process of preparing ethylene glycol by using shale gas.

SUMMARY OF THE INVENTION

An object of an embodiment of the invention is to provide a process for preparing formaldehyde which comprises forming the formaldehyde by reacting methanol with methanol in the presence of a catalyst composition comprising rhodium catalysts and ruthenium catalysts at a temperature of about 50-150° C. and a pressure of about 0-20 kg/cm$^2$G. In one embodiment, the step of forming the formaldehyde by reacting methanol with methanol further forms by-products being hydrogen ($H_2$) and carbon monoxide (CO) substantially without the formation of water. Preferably, the step of forming formaldehyde by reacting methanol with methanol is at a temperature of about 70-90° C. and a pressure of about 0-4 kg/cm$^2$G.

An object of an embodiment of the invention is to provide a process for preparing glycolaldehyde which comprises forming the glycolaldehyde by reacting formaldehyde with formaldehyde in the presence of a catalyst composition comprising rhodium catalysts and ruthenium catalysts at a temperature of about 50-150° C. and a pressure of about 0-20 kg/cm$^2$G. In one embodiment, the formaldehyde is anhydrous formaldehyde. Preferably, the step of forming glycolaldehyde by reacting formaldehyde with formaldehyde is at a temperature of about 90-110° C. and a pressure of about 2-6 kg/cm$^2$G.

An object of an embodiment of the invention is to provide a process for preparing ethylene glycol which comprises forming the ethylene glycol by reacting glycolaldehyde with hydrogen to hydrogenate the glycolaldehyde in the presence of a catalyst composition comprising rhodium catalysts and ruthenium catalysts at a temperature of about 50-150° C. and a pressure of about 5-50 kg/cm$^2$G. Preferably, the step of forming ethylene glycol by reacting glycolaldehyde with hydrogen to hydrogenate the glycolaldehyde is at a temperature of about 110-130° C. and a pressure of about 10-30 kg/cm$^2$G.

An object of an embodiment of the invention is to provide a process for preparing ethylene glycol which comprises forming the ethylene glycol by reacting methanol with methanol in the presence of a catalyst composition comprising rhodium catalysts and ruthenium catalysts at a temperature of about 50-150° C. and a pressure of about 0-40 kg/cm$^2$G. Preferably, the step of forming ethylene glycol by reacting methanol with methanol is at a temperature of about 110-130° C. and a pressure of about 2-10 kg/cm$^2$G.

An object of an embodiment of the invention is to provide a process for preparing ethylene glycol and formaldehyde which comprises forming the ethylene glycol and the formaldehyde by reacting glycolaldehyde with methanol in the presence of a catalyst composition comprising rhodium catalysts and ruthenium catalysts at a temperature of about 50-150° C. and a pressure of about 0-40 kg/cm$^2$G. Preferably, the step of forming ethylene glycol and formaldehyde by reacting glycolaldehyde with methanol is at a temperature of about 110-130° C. and a pressure of about 2-10 kg/cm$^2$G.

According to an embodiment of the invention, a special catalyst composition is successfully found that can be used in all of the above-mentioned processes. Since all of the above-mentioned processes can use a same catalyst composition comprising rhodium catalysts and ruthenium catalysts, the present process can make the reaction start in a same autoclave after the previous process is finished. In one embodiment, the ethylene glycol may be obtained by reacting methanol with methanol. Not only are the production steps simplified, but the production time is also reduced. Accordingly, the cost of ethylene glycol is remarkablely reduced.

BRIEF DESCRIPTION OF THE DRAWINGS

Detailed Description of the Invention

According to an embodiment of the invention, a multi-steps process using a plurality of steps to prepare ethylene glycol is provided which comprises the following steps: (a) a step for preparing formaldehyde; (b) a step for preparing glycolaldehyde and (c) a step for hydrogenating the glycolaldehyde to form the ethylene glycol. The above steps may be executed in different autoclaves or executed in a same autoclave at different times under different conditions. The detailed description of the above steps is presented as follows by using the following examples and comparative examples.

In the following examples and comparative examples, the experiments are executed in 250 ml of an autoclave in which magnetic mixers driven by a magnetic force are placed. Specifically, the autoclave is fed with 20 g of reactants, 20 g of ligand, 0.04 g of catalyst and 150 g of solvent of respective steps. In addition, the autoclave is optionally fed with 10 g of proton sponge, if necessary. Then, air in the autoclave is removed by hydrogen. The autoclave is pressurized to a reaction pressure of respective steps. The contents of the autoclave are then heated to reaction temperature of respective steps. The reaction of the reactants starts in the autoclave for a requested reaction time of respective steps. Upon completion of the reaction, the contents are cooled and the conversion of the reactants, yield of the products and selectivity to the products are determined.

According to an embodiment of the invention, a process for preparing formaldehyde which comprises forming the formaldehyde by reacting methanol ($CH_3OH$) with methanol is provided. The by-products of the process include hydrogen ($H_2$) and carbon monoxide (CO). Preferably, the by-products of the process substantially do not include water so that anhydrous formaldehyde is obtained.

Example 1

The autoclave is fed with 20 g of methanol. Formaldehyde is then obtained by reacting methanol with methanol for about 5 hours in the presence of diphenyl ether ($Ph_2O$) and a catalyst composition comprising rhodium catalysts and ruthenium catalysts at a temperature of about 80° C. and a pressure of about 2 kg/cm²G. In addition, the by-products being hydrogen ($H_2$) and carbon monoxide (CO) are simultaneously obtained. In example 1, the ruthenium catalysts may be 0.02 g of $HRuCl(CO)(PPh_3)_3$, and the rhodium catalysts may be 0.02 g of $HRh(CO)(PPh_3)_3$. The formaldehyde is produced according to the foregoing reaction equation.

Full Reaction

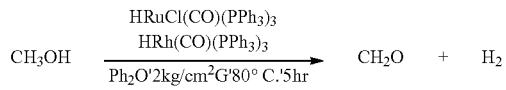

Vice Reaction

Upon completion of the reaction, the weights of the contents of the autoclave are measured and the conversion of the reactants, yield of the products and selectivity to the products are calculated. The obtained experiment results are as follows. The weight of methanol is reduced from 20 g to 5.2 g. The measured weight of formaldehyde is 13.2 g. The measured weight of carbon monoxide is 0.6 g. The conversion of methanol is about 74%. The yield of formaldehyde is about 70%. The selectivity to formaldehyde is about 95%, and the selectivity to carbon monoxide is about 5%.

Note that, the temperature and pressure of example 1 are merely shown as an example. According to an embodiment of the invention, the step of forming the formaldehyde may be executed in any appropriate temperature and pressure. For instance, the temperature preferably is about 50-150° C., most preferably about 70-90° C., and the pressure preferably is about 0-20 kg/cm²G, most preferably about 0-4 kg/cm²G.

Comparative Example 1

The autoclave is fed with 20 g of methanol. Formaldehyde is then obtained by reacting methanol with methanol for about 5 hours in the presence of diphenyl ether ($Ph_2O$) and ruthenium catalysts at a temperature of about 80° C. and a pressure of about 2 kg/cm²G. In addition, the by-products being hydrogen ($H_2$) and carbon monoxide (CO) are simultaneously obtained. In comparative example 1, the ruthenium catalysts may be 0.04 g of $HRuCl(CO)(PPh_3)_3$.

Upon completion of the reaction, the weights of the contents of the autoclave are measured and the conversion of the reactants, yield of the products and selectivity to the products are calculated. The obtained experiment results are as follows. The weight of methanol is reduced from 20 g to 6.2 g. The measured weight of formaldehyde is 11.6 g. The measured weight of carbon monoxide is 1.2 g. The conversion of methanol is about 69%. The yield of formaldehyde is about 62%. The selectivity to formaldehyde is about 90%, and the selectivity to carbon monoxide is about 10%.

In addition, in order to prove that the catalytic effect of the mixture of rhodium catalysts and ruthenium catalysts surpasses the catalytic effect of a single kind of catalyst, the inventors further conduct experiments of comparative examples 1A, 1B and 10. Comparative examples 1A uses 0.04 g of $IrCl(CO)(PPh_3)_2$ as catalyst. Comparative examples 1B uses 0.04 g of $HRh(CO)(PPh_3)_3$ as catalyst. Comparative examples 1C uses 0.04 g of $Pd(PPh_3)_4$ as catalyst. Upon completion of the reaction, the weights of the contents of the autoclave are measured and the conversion of the reactants, yield of the products and selectivity to the products are calculated. In order to make it easier to compare the effect of example 1 with the effects of comparative examples 1A-1C, the experiment data are listed in table 1. According to table 1, it is shown that the effect and yield of example 1 surpass the effects and yields of comparative example 1A-1C.

TABLE 1

| Item | Catalyst | Field A | Field B | Field C | Field D | Field E | Field F | Field G |
|---|---|---|---|---|---|---|---|---|
| example 1 | $HRuCl(CO)(PPh_3)_3$ $HRh(CO)(PPh_3)_3$ | 5.2 | 74 | 13.2 | 95 | 0.6 | 5 | 70 |
| comparative example 1 | $HRuCl(CO)(PPh_3)_3$ | 6.2 | 69 | 11.6 | 90 | 1.2 | 10 | 62 |
| comparative example 1A | $IrCl(CO)(PPh_3)_2$ | 2.8 | 86 | 9.9 | 61 | 5.7 | 38 | 53 |

TABLE 1-continued

| Item | Catalyst | Field A | Field B | Field C | Field D | Field E | Field F | Field G |
|---|---|---|---|---|---|---|---|---|
| comparative example 1B | HRh(CO)(PPh$_3$)$_3$ | 10.8 | 46 | 7.9 | 92 | 0.6 | 7 | 42 |
| comparative example 1C | Pd(PPh$_3$)$_4$ | 13.8 | 31 | 5.4 | 93 | 0.3 | 6 | 29 |

1. Field A indicates the weight of methanol (g). Field B indicates the conversion of methanol (%). Field C indicates the weight of formaldehyde (g). Field D indicates the selectivity to formaldehyde (%). Field E indicates the weight of carbon monoxide (g). Field F indicates the selectivity to carbon monoxide (%). Field G indicates the yield of formaldehyde (%).

In addition, in example 1, the formed products substantially do not include water so that anhydrous formaldehyde may be directly formed. Compare with the prior art, the distillation of a mixture of water and formaldehyde to obtain anhydrous formaldehyde is not needed. Accordingly, the production steps for preparing ethylene glycol may be simplified and the cost of ethylene glycol may be also reduced.

Example 2

The autoclave is fed with 20 g of formaldehyde, preferably, anhydrous formaldehyde. Glycolaldehyde is then obtained by reacting formaldehyde with formaldehyde (preferably, anhydrous formaldehyde) for about 5 hours in the presence of diphenyl ether (Ph$_2$O) and a catalyst composition comprising rhodium catalysts and ruthenium catalysts at a temperature of about 100° C. and a pressure of about 4 kg/cm$^2$G. In addition, the by-products being carbon monoxide (CO) is simultaneously obtained. In example 2, the ruthenium catalysts may be 0.02 g of HRuCl(CO)(PPh$_3$)$_3$, and the rhodium catalysts may be 0.02 g of HRh(CO)(PPh$_3$)$_3$. The glycolaldehyde is produced according to the foregoing reaction equation.
Full Reaction

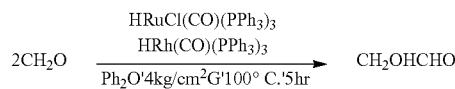

Upon completion of the reaction, the weights of the contents of the autoclave are measured and the conversion of the reactants, yield of the products and selectivity to the products are calculated. The obtained experiment results are as follows. The weight of formaldehyde is reduced from 20 g to 5.4 g. The measured weight of glycolaldehyde is 13.7 g. The measured weight of carbon monoxide is 0.5 g. The conversion of formaldehyde is about 73%. The yield of glycolaldehyde is about 69%. The selectivity to glycolaldehyde is about 94%, and the selectivity to carbon monoxide is about 4%.

Note that, the temperature and pressure of example 2 are merely shown as an example. According to an embodiment of the invention, the step of forming the glycolaldehyde may be executed in any appropriate temperature and pressure. For instance, the temperature preferably is about 50-150° C., most preferably about 90-110° C., and the pressure preferably is about 0-20 kg/cm$^2$G, most preferably about 2-6 kg/cm$^2$G.

Comparative Example 2

The autoclave is fed with 20 g of formaldehyde. Glycolaldehyde is then obtained by reacting formaldehyde with formaldehyde (preferably, anhydrous formaldehyde) for about 5 hours in the presence of N,N-dimethylacetamide (DMAC) and rhodium catalysts at a temperature of about 100° C. and a pressure of about 4 kg/cm$^2$G. In addition, the by-products being carbon monoxide (CO) is simultaneously obtained. In comparative example 2, the rhodium catalysts may be 0.04 g of HRh(CO)(PPh$_3$)$_3$.

Upon completion of the reaction, the weights of the contents of the autoclave are measured and the conversion of the reactants, yield of the products and selectivity to the products are calculated. The obtained experiment results are as follows. The weight of formaldehyde is reduced from 20 g to 9.2 g. The measured weight of glycolaldehyde is 10.0 g. The measured weight of carbon monoxide is 0.6 g. The conversion of formaldehyde is about 54%. The yield of glycolaldehyde is about 50%. The selectivity to glycolaldehyde is about 93%, and the selectivity to carbon monoxide is about 6%. In order to make it easier to compare the effect of example 2 with the effect of comparative example 2, the experiment data are listed in table 2. According to table 2, it is shown that the effect and yield of example 2 surpass the effect and yield of comparative example 2.

TABLE 2

| Item | Catalyst | Field A | Field B | Field C | Field D | Field E | Field F | Field G |
|---|---|---|---|---|---|---|---|---|
| example 2 | HRuCl(CO)(PPh$_3$)$_3$ HRh(CO)(PPh$_3$)$_3$ | 5.4 | 73 | 13.7 | 94 | 0.5 | 4 | 69 |
| comparative example 2 | HRuCl(CO)(PPh$_3$)$_3$ | 9.2 | 54 | 10.0 | 93 | 0.6 | 6 | 50 |

1. Field A indicates the weight of formaldehyde (g). Field B indicates the conversion of formaldehyde (%). Field C indicates the weight of glycolaldehyde (g). Field D indicates the selectivity to glycolaldehyde (%). Field E indicates the weight of carbon monoxide (g). Field F indicates the selectivity to carbon monoxide (%). Field G indicates the yield of glycolaldehyde (%).

Example 3

The autoclave is fed with 20 g of glycolaldehyde and an appropriate amount of hydrogen. Ethylene glycol is then obtained by hydrogenating the glycolaldehyde for about 5 hours in the presence of diphenyl ether (Ph$_2$O) and a catalyst composition comprising rhodium catalysts and ruthenium catalysts at a temperature of about 120° C. and a pressure of about 20 kg/cm$^2$G. In example 3, the ruthenium catalysts may be 0.02 g of HRuCl(CO)(PPh$_3$)$_3$, and the rhodium catalysts may be 0.02 g of HRh(CO)(PPh$_3$)$_3$. The step of hydrogenating the glycolaldehyde is executed according to the foregoing reaction equation.

Full Reaction

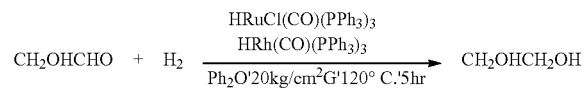

Upon completion of the reaction, the weights of the contents of the autoclave are measured and the conversion of the reactants, yield of the products and selectivity to the products are calculated. The obtained experiment results are as follows. The weight of glycolaldehyde is reduced from 20 g to 1.4 g. The measured weight of ethylene glycol is 18.6 g. The conversion of glycolaldehyde is about 93%. The yield of ethylene glycol is about 90%. The selectivity to ethylene glycol is about 97%.

Note that, the temperature and pressure of example 3 are merely shown as an example. According to an embodiment of the invention, the step of hydrogenating glycolaldehyde may be executed in any appropriate temperature and pressure. For instance, the temperature preferably is about 50-150° C., most preferably about 110-130° C., and the pressure preferably is about 5-50 kg/cm$^2$G, most preferably about 10-30 kg/cm$^2$G.

Comparative Example 3

The autoclave is fed with 20 g of glycolaldehyde and an appropriate amount of hydrogen. Ethylene glycol is then obtained by hydrogenating glycolaldehyde for about 5 hours in the presence of N,N-dimethylacetamide and ruthenium catalysts at a temperature of about 120° C. and a pressure of about 20 kg/cm$^2$G. In comparative example 3, the ruthenium catalysts may be 0.04 g of HRuCl(CO)(PPh$_3$)$_3$.

Upon completion of the reaction, the weights of the contents of the autoclave are measured and the conversion of the reactants, yield of the products and selectivity to the products are calculated. The obtained experiment results are as follows. The weight of glycolaldehyde is reduced from 20 g to 2.0 g. The measured weight of ethylene glycol is 16.6 g. The conversion of glycolaldehyde is about 90%. The yield of ethylene glycol is about 80%. The selectivity to ethylene glycol is about 89%.

In order to make it easier to compare the effect of example 3 with the effect of comparative example 3, the experiment data are listed in table 3. According to table 3, it is shown that the effect and yield of example 3 surpass the effect and yield of comparative example 3.

TABLE 3

| Item | Catalyst | Field A | Field B | Field C | Field D | Field E |
|---|---|---|---|---|---|---|
| example 3 | HRuCl(CO) (PPh$_3$)$_3$ HRh(CO) (PPh$_3$)$_3$ | 1.4 | 9.3 | 18.6 | 97 | 90 |
| comparative example 3 | HRuCl(CO) (PPh$_3$)$_3$ | 2.0 | 90 | 16.6 | 89 | 80 |

1. Field A indicates the weight of glycolaldehyde (g). Field B indicates the conversion of glycolaldehyde (%). Field C indicates the weight of ehylene glycol (g). Field D indicates the selectivity to ehylene glycol (%). Field E indicates the yield of ehylene glycol (%).

According to an embodiment of the invention, a one-step process for preparing ethylene glycol is provided. The above multi-steps process for preparing ethylene glycol is divided into a plurality of steps which form intermediums and then prepare ethylene glycol from the intermediums. In contrast to the above multi-steps process, the one-step process for preparing ethylene glycol does not need to be divided into a plurality of steps, and ethylene glycol may be formed by reacting methanol with methanol in a same autoclave in the presence of a specific catalyst composition at an appropriate temperature and an appropriate pressure.

Example 4

The autoclave is fed with 20 g of methanol. Ethylene glycol is then obtained by reacting methanol with methanol for about 5 hours in the presence of diphenyl ether (Ph$_2$O) and a catalyst composition comprising rhodium catalysts and ruthenium catalysts at a temperature of about 120° C. and a pressure of about 6 kg/cm$^2$G. In addition, the by-product being hydrogen (H$_2$) is simultaneously obtained. In example 4, the ruthenium catalysts may be 0.04 g of HRuCl(CO)(PPh$_3$)$_3$, and the rhodium catalysts may be 0.04 g of HRh(CO)(PPh$_3$)$_3$. The one-step process for preparing ethylene glycol is executed according to the foregoing reaction equation.

Full Reaction

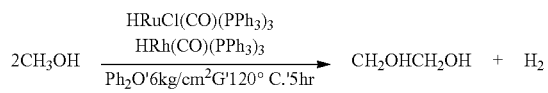

Upon completion of the reaction, the weights of the contents of the autoclave are measured and the conversion of the reactants, yield of the products and selectivity to the products are calculated. The obtained experiment results are as follows. The weight of methanol is reduced from 20 g to 6.0 g. The measured weight of ethylene glycol is 11.7 g. The conversion of methanol is about 70%. The yield of ethylene glycol is about 60%. The selectivity to ethylene glycol is about 86%.

Note that, the temperature and pressure of example 4 are merely shown as an example. According to an embodiment of the invention, the one-step process for preparing ethylene glycol may be executed in any appropriate temperature and pressure. For instance, the temperature preferably is about 50-150° C., most preferably about 110-130° C., and the pressure preferably is about 0-40 kg/cm$^2$G, most preferably about 2-10 kg/cm$^2$G.

Comparative Example 4

The autoclave is fed with 20 g of methanol. Hydrogen (H$_2$) and carbon monoxide (CO) are then obtained by reacting methanol with methanol for about 2 hours in the presence of cumene and a mixture of rhodium catalysts and ruthenium catalysts at a temperature of about 150° C. and a pressure of about 0 kg/cm$^2$G. In comparative example 4, the ruthenium catalysts may be 0.02 g of HRuCl(CO)(PPh$_3$)$_3$, and the rhodium catalysts may be 0.02 g of HRh(CO)(PPh$_3$)$_3$. The reaction equation under the condition of comparative example 4 is as the foregoing reaction equation.

Full Reaction

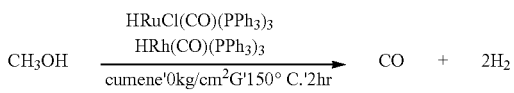

Upon completion of the reaction, the weights of the contents of the autoclave are measured and the conversion of the reactants, yield of the products and selectivity to the products are calculated. The obtained experiment results are as follows. The weight of methanol is reduced from 20 g to 5.8 g. The measured weight of carbon monoxide is 10.1 g. The conversion of methanol is about 71%. The selectivity to carbon monoxide is about 81%, the yield of carbon monoxide is about 58%. In contrast to example 4, comparative example 4 mainly executes the vice reaction of example 1 as opposed to the main reaction of example 4 or 1. Accordingly, the yield of ethylene glycol of example 4 surpasses the yield of ethylene glycol of comparative example 4.

According to the prior art, ethylene glycol is obtained by reacting hydrogen with glycolaldehyde to hydrogenate the glycolaldehyde. In contrast to the prior art, a process for preparing ethylene glycol and formaldehyde in one embodiment of the invention does not use hydrogen to hydrogenate the glycolaldehyde. Indeed, the ethylene glycol and formaldehyde are obtained by reacting methanol with glycolaldehyde. According to the above process for preparing ethylene glycol and formaldehyde, not only is ethylene glycol formed, but also formaldehyde is formed which is an intermedium of multi-steps process for preparing ethylene glycol and can be used to prepare glycolaldehyde.

Example 5

The autoclave is fed with 20 g of glycolaldehyde and 10 g of methanol. Ethylene glycol and formaldehyde are then obtained by reacting methanol with glycolaldehyde for about 5 hours in the presence of diphenyl ether ($Ph_2O$) and a catalyst composition comprising rhodium catalysts and ruthenium catalysts at a temperature of about 120° C. and a pressure of about 6 $kg/cm^2G$. In example 5, the ruthenium catalysts may be 0.02 g of $HRuCl(CO)(PPh_3)_3$, and the rhodium catalysts may be 0.02 g of $HRh(CO)(PPh_3)_3$. The process for preparing ethylene glycol and formaldehyde is executed according to the foregoing reaction equation.
Full Reaction

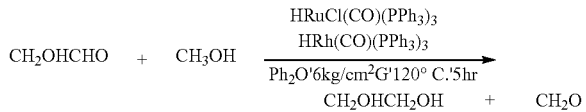

Upon completion of the reaction, the weights of the contents of the autoclave are measured and the conversion of the reactants, yield of the products and selectivity to the products are calculated. The obtained experiment results are as follows. The weight of glycolaldehyde is reduced from 20 g to 8.2 g. The weight of methanol is reduced from 10 g to 2.8 g. The measured weight of ethylene glycol is 14.1 g. The measured weight of formaldehyde is 4.1 g. The conversion of glycolaldehyde is about 59%. The conversion of methanol is about 72%. The yield of ethylene glycol is about 68%. The yield of formaldehyde is about 44%. The selectivity to ethylene glycol is about 116%, and the selectivity to formaldehyde is about 61%.

Note that, the temperature and pressure of example 5 are merely shown as an example. According to an embodiment of the invention, the step of forming the ethylene glycol and formaldehyde may be executed in any appropriate temperature and pressure. For instance, the temperature preferably is about 50-150° C., most preferably about 110-130° C., and the pressure preferably is about 0-40 $kg/cm^2G$, most preferably about 2-10 $kg/cm^2G$.

Comparative Example 5

In an embodiment of the invention, example 5 may not use a catalyst composition comprising rhodium catalysts and ruthenium catalysts and only use rhodium catalysts to catalyze the reaction.

The autoclave is fed with 20 g of glycolaldehyde and 10 g of methanol. Ethylene glycol and formaldehyde are then obtained by reacting glycolaldehyde with methanol for about 5 hours in the presence of diphenyl ether ($Ph_2O$) and a single kind of catalyst being ruthenium catalysts at a temperature of about 120° C. and a pressure of about 6 $kg/cm^2G$. In comparative example 5, the ruthenium catalysts may be 0.04 g of $HRuCl(CO)(PPh_3)_3$. The step of forming the ethylene glycol and formaldehyde is executed according to a reaction equation same with that of example 5.

Upon completion of the reaction, the weights of the contents of the autoclave are measured and the conversion of the reactants, yield of the products and selectivity to the products are calculated. The obtained experiment results are as follows. The weight of glycolaldehyde is reduced from 20 g to 7.4 g. The weight of methanol is reduced from 10 g to 3.5 g. The measured weight of ethylene glycol is 12.6 g. The measured weight of formaldehyde is 5.5 g. The conversion of glycolaldehyde is about 63%. The conversion of methanol is about 65%. The yield of ethylene glycol is about 61%. The yield of formaldehyde is about 59%. The selectivity to ethylene glycol is about 97%, and the selectivity to formaldehyde is about 90%.

Compare example 5 with comparative example 5, the 68% of yield and 116% of selectivity of ethylene glycol of example 5 are greater than the 61% of yield and 97% of selectivity of ethylene glycol of comparative example 5. It is proven that the catalytic effect of a mixture of rhodium catalysts and ruthenium catalysts surpasses the catalytic effect of ruthenium catalysts.

In addition, since the products of example 5 and comparative example 5 are ethylene glycol or formaldehyde which is an intermedium for preparing ethylene glycol, the effective yield and selectivity of the products of example 5 and comparative example 5 surpass that of example 3 and the traditional process for hydrogenating glycolaldehyde.

According to the present invention, the solvent does not limited to any specific type of solvent, and it may be, for example, aromatic ethers, amides, aromatic alkyl, aromatic amines and the like.

The above examples use triphenylphosphine ($PPh_3$) as a ligand. However, the present invention is not limited thereto, and any currently existing or future developed ligand may be used.

In addition, in one embodiment, the rhodium catalysts and ruthenium catalysts are preferably organic rhodium catalysts and organic ruthenium catalysts. In one embodiment, the organic rhodium catalysts and organic ruthenium catalysts include an phosphine ligand. In one embodiment the organic ruthenium catalysts are divalent ruthenium carbonyl complex catalysts.

In an embodiment, the organic rhodium catalysts including an phosphine ligand may include a source of rhodium, and a ligand of general formula $R^1P$—$R_2$ (I), wherein $R^1$ is a bivalent radical that together with the phosphorous atom to which it is attached is an optionally substituted 2-phospha-tricyclo [3.3.1.1$\{3,7\}$]-decyl group, wherein from 1 to 5 of the carbon atoms have been replaced by a heteroatom, and wherein $R^2$ is a monovalent radical which is an optionally substituted hydrocarbyl group having from 1 to 40 carbon atoms. Preferably, the bivalent radical $R^1$ together with the phosphorous atom to which it is attached is a 2-phospha-1,3,5,7-tetralkyl-6,9,10-trioxa-tricyclo[3.3.1.1 $\{3,7\}$]-decyl group. The monovalent radical $R^2$ is of the general formula —$R^3$—C(O) $NR^4R^5$, wherein $R^3$ is an alkylene group and $R^4$ and $R^5$ independently represent an alkyl, cycloalkyl, aryl or alkaryl group, or $R^4$ and $R^5$ together represent a bivalent bridging group.

In an embodiment, the organic ruthenium catalysts have the general formula: $Ru(CO)HA(Z)_3$, wherein A is a halogen atom, most preferably chlorine, or a hydrogen atom and Z is —$PR^1R^2R^3$ in which $R^1$, $R^2$ and R preferably$^3$ are the same or different and are selected from alkyl and aryl groups, all the phenyl group. In an embodiment of the invention, the organic ruthenium catalysts have the general formula: $Ru(CO)XY(Z)_2$, wherein X is a carboxylate group, particularly $ClCH_2OOO$—, $Cl_2CHCOO$—, $Cl_3CCOO$—, $F_3CCOO$—, $CH_3COO$—, $C_6H_5COO$— or p-$ClC_6H_4COO$—, y is a halogen atom, preferably a chlorine atom or a bromine atom, or a hydrogen atom or a carboxylate group, Z is as defined above.

According to an embodiment of the invention, ethylene glycol is obtained by respectively executing the processes of examples 1, 2 and 3. Compare with the prior art, since anhydrous formaldehyde may be directly formed, the distillation of a mixture of water and formaldehyde in the conventional process may be omitted, so that not only are the production steps simplified, but also the cost of preparing ethylene glycol is reduced. Accordingly, the total yield and production cost of ethylene glycol of the present invention surpass that of the conventional process.

According to an embodiment of the invention, a specific catalyst composition comprising rhodium catalysts and ruthenium catalysts is successfully found which may be simultaneously used in the processes of examples 1, 2 and 3. Since the processes of examples 1, 2 and 3 use a same catalyst composition comprising rhodium catalysts and ruthenium catalysts, upon completion of the reaction of example 1, the reaction of example 2 may directly start after hydrogen ($H_2$) and carbon monoxide (CO) are removed from the autoclave. In an embodiment, upon completion of the reaction of example 2, the reaction of example 3 may also directly start after hydrogen ($H_2$) is fed into the autoclave.

According to the prior art, since different steps use different catalysts, the processes in the different steps cannot be executed in a same autoclave, without clearing, to avoid the contamination between the different catalysts. Compare with the prior art, the processes of examples 1, 2 and 3 can be executed in a same autoclave at different times under different conditions since they all use a same catalyst composition. Accordingly, not only are the production steps simplified, but also the cost of preparing ethylene glycol is reduced.

In ideal conditions, the total reaction time to obtain ethylene glycol is about 15 hours according to examples 1-3. The reaction time of the one-step process for preparing ethylene glycol by directly reacting methanol with methanol according to example 4 is only about 5 hours. Not only are the production steps simplified, but also the reaction time is reduced and the cost of preparing ethylene glycol is remarkablely reduced.

As described above, according to the present invention, the conventional process for preparing ethylene glycol is improved, and the production cost of ethylene glycol can be reduced.

What is claimed is:

1. A process for preparing glycolaldehyde comprising:
   forming the glycolaldehyde by reacting formaldehyde with formaldehyde in the presence of a catalyst composition comprising rhodium catalysts and ruthenium catalysts at a temperature of about 50-150° C. and a pressure of about 0-20 kg/cm$^2$G.

2. The process according to claim 1, wherein the formaldehyde is anhydrous formaldehyde.

3. The process according to claim 1, wherein:
   the step of forming the glycolaldehyde by reacting formaldehyde with formaldehyde is executed at the temperature of about 90-110° C. and the pressure of about 2-6 kg/cm$^2$G.

4. A process for preparing ethylene glycol comprising:
   forming the ethylene glycol by reacting methanol with methanol in the presence of a catalyst composition comprising rhodium catalysts and ruthenium catalysts at a temperature of about 50-150° C. and a pressure of about 0-40 kg/cm$^2$G.

5. The process according to claim 4, wherein:
   the step of forming the ethylene glycol by reacting methanol with methanol is executed at the temperature of about 110-130° C. and the pressure of about 2-10 kg/cm$^2$G.

6. A process for preparing ethylene glycol and formaldehyde comprising:
   forming the ethylene glycol and formaldehyde by reacting glycolaldehyde with methanol in the presence of a catalyst composition comprising rhodium catalysts and ruthenium catalysts at a temperature of about 50-150° C. and a pressure of about 0-40 kg/cm$^2$G.

7. The process according to claim 6, wherein:
   the step of forming the ethylene glycol and formaldehyde by reacting glycolaldehyde with methanol is executed at the temperature of about 110-130° C. and the pressure of about 2-10 kg/cm$^2$G.

* * * * *